United States Patent
Baker et al.

(10) Patent No.: US 7,276,229 B1
(45) Date of Patent: Oct. 2, 2007

(54) ORAL COMPOSITIONS COMPRISING A VISCOSITY MODIFIER FOR REDUCTION OF TOOTH EROSION

(75) Inventors: Nicola Jane Baker, Thetford (GB); David Myatt Parker, Hereford (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 0 days.

(21) Appl. No.: 09/786,492

(22) PCT Filed: Aug. 31, 1999

(86) PCT No.: PCT/EP99/06423

§ 371 (c)(1), (2), (4) Date: Jun. 20, 2002

(87) PCT Pub. No.: WO00/13531

PCT Pub. Date: Mar. 16, 2000

(30) Foreign Application Priority Data

Sep. 9, 1998 (GB) ................. 9819530.8

(51) Int. Cl.
- A61K 8/00 (2006.01)
- A61K 8/18 (2006.01)
- A61Q 11/00 (2006.01)
- A23L 2/00 (2006.01)
- A23L 2/38 (2006.01)

(52) U.S. Cl. ............ 424/49; 424/58; 426/590; 426/599; 433/217.1; 514/901

(58) Field of Classification Search ............. 424/49; 514/54, 835, 901; 433/217.1, 228.1; 426/590, 426/599

See application file for complete search history.

(56) References Cited

U.S. PATENT DOCUMENTS

| | | | |
|---|---|---|---|
| 2,943,941 A * | 7/1960 | Gray et al. ............. 426/12 |
| 3,681,091 A | 8/1972 | Kohl et al. ............. 426/532 |
| 3,894,147 A | 7/1975 | Bahouth et al. ......... 424/57 |
| 3,968,263 A | 7/1976 | Reussner .............. 426/590 |
| 4,080,440 A | 3/1978 | DiGiulio et al. ........ 424/49 |
| 4,143,172 A | 3/1979 | Mitchell et al. ........ 426/532 |
| 4,163,069 A | 7/1979 | Melachouris et al. .... 426/582 |
| 4,219,583 A | 8/1980 | Igoe .................. 426/580 |
| 4,255,414 A | 3/1981 | Lembke et al. .......... 424/50 |
| 4,322,407 A | 3/1982 | Ko .................... 424/128 |
| 4,349,533 A | 9/1982 | Dent et al. ............ 424/52 |
| 4,551,342 A | 11/1985 | Nakel et al. |
| 4,722,847 A * | 2/1988 | Heckert ............... 426/74 |
| 4,737,375 A | 4/1988 | Nakel et al. |
| 4,772,467 A | 9/1988 | Pak et al. |
| 4,830,862 A | 5/1989 | Braun et al. |
| 4,851,221 A | 7/1989 | Pak et al. |
| 4,885,155 A | 12/1989 | Parrar, Jr. et al. ...... 424/52 |
| 4,906,482 A | 3/1990 | Zemel et al. ........... 426/74 |
| 4,919,963 A | 4/1990 | Heckert et al. |
| 4,935,225 A | 6/1990 | Curtis et al. ........... 424/49 |
| 4,943,443 A | 7/1990 | Evers ................. 426/569 |
| 4,980,182 A | 12/1990 | Kwon et al. ........... 426/130 |
| 5,017,362 A | 5/1991 | Gaffar et al. .......... 424/52 |
| 5,021,251 A | 6/1991 | McKenna et al. ....... 426/330.5 |
| 5,028,446 A | 7/1991 | Saleeb et al. |
| 5,064,640 A | 11/1991 | Kleber et al. .......... 424/52 |
| 5,094,870 A | 3/1992 | Scaglione et al. ....... 426/549 |
| 5,096,701 A | 3/1992 | White et al. ........... 424/52 |
| 5,108,761 A | 4/1992 | Andon et al. |
| 5,244,684 A | 9/1993 | Tong et al. ........... 426/330.5 |
| 5,336,510 A | 8/1994 | Chang ................ 426/72 |
| 5,417,994 A | 5/1995 | Chang et al. .......... 426/330.3 |
| 5,424,082 A | 6/1995 | Dake et al. |
| 5,431,940 A | 7/1995 | Calderas et al. ....... 426/330.5 |
| 5,445,837 A | 8/1995 | Burkes et al. |
| 5,468,506 A | 11/1995 | Andon |
| 5,474,793 A | 12/1995 | Meyer et al. |
| 5,500,232 A | 3/1996 | Keating |
| 5,597,595 A | 1/1997 | DeWille et al. |
| 5,609,904 A | 3/1997 | Koh et al. ............ 426/565 |
| 5,641,532 A | 6/1997 | Pflaumer et al. ....... 426/590 |
| 5,654,027 A | 8/1997 | Chalupa .............. 426/573 |
| 5,690,975 A | 11/1997 | Akahoski et al. |
| 5,792,502 A * | 8/1998 | Montezinos ........... 426/590 |

(Continued)

FOREIGN PATENT DOCUMENTS

EP 40654 12/1981

(Continued)

OTHER PUBLICATIONS

Reijden et al., "Influence of Polymers for Use in Saliva Substitutes on De- and Remineralization of Enamel in vitro", Caries Research, 1997, 31, pp. 216-223.

(Continued)

*Primary Examiner*—Frederick Krass
(74) *Attorney, Agent, or Firm*—Dara L. Dinner; Theodore R. Furman; Charles M. Kinzig

(57) ABSTRACT

The use of viscosity modifying polymer materials, commonly used as stabilisers, thickeners and emulsifiers, as tooth erosion inhibitors in acidic compositions for oral administration, especially in acidic beverages such as fruit drinks and oral healthcare products such as mouthwashes, in which the effective pH of the composition is less than or equal to 4.5.

37 Claims, No Drawings

U.S. PATENT DOCUMENTS

| | | | |
|---|---|---|---|
| 5,817,351 A | 10/1998 | DeWille et al. | |
| 5,827,505 A | 10/1998 | Hughes et al. | 424/49 |
| 5,833,957 A | 11/1998 | Winston et al. | 424/49 |
| 5,834,045 A | 11/1998 | Keating et al. | |
| 5,866,102 A | 2/1999 | Winston et al. | 424/52 |
| 5,866,190 A | 2/1999 | Barey | |
| 5,885,553 A | 3/1999 | Michael | 424/49 |
| 5,891,888 A | 4/1999 | Strahl | 514/305 |
| 5,919,512 A | 7/1999 | Montezinos et al. | 426/590 |
| 5,939,052 A | 8/1999 | White et al. | 424/52 |
| 5,955,136 A | 9/1999 | Laaman et al. | 426/569 |
| 6,022,576 A | 2/2000 | Cirigliano et al. | 426/597 |
| 6,036,986 A | 3/2000 | Cirigliano et al. | 426/330.5 |
| 6,039,987 A | 3/2000 | Strahl | 426/76 |
| 6,051,200 A | 4/2000 | Glascock et al. | 423/309 |
| 6,056,984 A | 5/2000 | Ekanayake et al. | 426/120 |
| 6,056,989 A | 5/2000 | Sasagawa et al. | 426/590 |
| 6,060,103 A | 5/2000 | Dunagan | 436/580 |
| 6,106,883 A | 8/2000 | Sokolik et al. | 426/573 |
| 6,126,980 A | 10/2000 | Smith et al. | 426/330.3 |
| 6,139,895 A | 10/2000 | Zablocki et al. | 426/573 |
| 6,159,448 A | 12/2000 | Winston et al. | |
| 6,187,295 B1 | 2/2001 | Glandorf | 424/52 |
| 6,190,644 B1 | 2/2001 | McClanahan | |
| 6,261,619 B1 | 7/2001 | Calderas et al. | 426/330.3 |
| 6,268,003 B1 | 7/2001 | Calderas et al. | 426/330.3 |
| 6,294,214 B1 | 9/2001 | Calderas et al. | 426/330.3 |
| 6,319,490 B1 * | 11/2001 | Parker | 424/55 |
| 6,326,040 B1 | 12/2001 | Kearney et al. | 426/271 |
| 6,383,473 B1 | 5/2002 | Parker | 424/49 |
| 6,440,482 B1 | 8/2002 | Henson et al. | 426/590 |
| 6,468,576 B1 | 10/2002 | Sher et al. | 426/565 |
| 6,719,963 B2 * | 4/2004 | Parker | 424/49 |
| 6,908,909 B2 | 6/2005 | Parker | 424/49 |
| 6,984,376 B2 | 1/2006 | Stephenson et al. | 424/49 |
| 2001/0051136 A1 | 12/2001 | Winston et al. | |
| 2004/0097517 A1 | 5/2004 | Baker et al. | 424/49 |

FOREIGN PATENT DOCUMENTS

| | | |
|---|---|---|
| EP | 223 762 | 5/1987 |
| EP | 0 587 972 | 3/1994 |
| EP | 0 719 783 | 8/1995 |
| EP | 845217 | 6/1998 |
| FR | 2 731 588 | 3/1995 |
| FR | A 2 731 588 | 3/1995 |
| GB | 1 250 535 | 3/1969 |
| GB | 1 516 525 | 10/1975 |
| GB | 1541461 | 2/1979 |
| GB | 2 207 335 | 2/1989 |
| JP | 61036211 | 2/1986 |
| JP | 62294607 | 12/1987 |
| JP | 04139120 | 5/1992 |
| JP | 05139979 | 8/1993 |
| JP | 09-295942 | 11/1997 |
| WO | WO97/21336 | 6/1997 |
| WO | WO 97/30601 | 8/1997 |
| WO | WO97/30601 * | 8/1997 |
| WO | WO 00/13531 | 3/2000 |
| WO | WO 01/00048 | 1/2001 |

OTHER PUBLICATIONS

Abstract of Muhler et al., South African 6904743, Heaplus, Abstract 469862 (1970).
Andlaw et al., Community Denistry and Oral Epidemiol., vol. 3, pp. 143-147 (1983).
Borggreven et al., Caries Research, vol. 26, pp. 84-88 (1992).
Clerehugh et al., American Journal of Dentistry, vol. 2, Special Issue, pp. 221-224 (1989).
DeShazer et al., Archs Oral Biol, vol. 13, pp. 1163-1165 (1968).
Harris, et al., J. Dent. Res., vol. 46(1) pp. 290-294 (1967).
Ingram et al., Caries Research, vol. 11, pp. 30-38 (1977).
Ingram, et al., Adv. Dent Res., vol. 8(2), pp. 158-165 (1994).
Larsen, Scandinavia Journal of Dentistry Research, vol. 83, pp. 13-17 (1975).
McGaughey et al., Journal of Densitry Research, vol. 56(6), pp. 579-587 (1977).
McGaughey, Caries Research, vol. 17, pp. 229-241 (1983).
Mor et al., New Zealand Dental Journal, vol. 77, pp. 57-61 (1981).
Newesly, Caries Research, vol. 1, pp. 1-14 (1967).
O'Mullane et al., J. Dent.Research, vol. 76(11), pp. 1776-1781 (1997).
Reussner er al., Journal of Dentistry Reseach, vol. 54(2), pp. 365-370 (1975).
Roberts, Adv. Dent. Res., vol. 9(3), pp. 304-311 (1995).
Shaw, J. Dent. Research, vol. 59(3), pp. 644-650 (1980).
Shibata et al., Archs. Oral Biol., vol. 27, pp. 809-816 (1982).
Stadtler, et al., Caries Research, vol. 30, pp. 418-422 (1996).
Stephen et al., International Dental Journal, vol. 44, #3, Supplement 1, pp. 287-295 (1994).
Stookey et al., J. Dent. Research, vol. 59(5), pp. 838-843 (1980).
*The Effect of Phosphates in Breakfast Cereals on Dental Caries*, Nutrition Review, vol. 25(9), pp. 263-265 (1967).
Bartels, et al., J of Dentistry, vol. 7(3) pp. 221-229 (1979).
Dawes, J of the Candian Dental Association, vol. 69(11) pp. 722-724 (2003).
Davis, et al., British Dental Journal, vol. 143 pp. 116-119 (1977).
EP Opposition to EP99946084.3 Submission of Aug. 26, 2004.
Hughes et al., Journal of Dentistry, 1999(27), pp. 285-289.
Hughes et al., Journal of Dentistry, 1999(27), pp. 345-350.
Hughes et al., Journal of Dentistry, 2000(28), pp. 147-152.
Lussi et al., Caries Res, 1993, 27(5), pp. 387-393.
Lussi et al., Caries Res, 1995, 29(5) pp. 349-354.
Parker, et al., European J of Oral Sciences, vol. 111 pp. 428-433 (2003).
Pearce, Calcif. Tissue Int., vol. 33 pp. 395-402 (1981).
Rugg-Gunn et al., Caries Research, 1998(32), pp. 337-343.
Schaad, et al., J of Colloid and Interface Science, vol. 164 pp. 291-295 (1994).
Thomann, et al., Colloids and Surfaces, vol. 54, pp. 145-159 (1991).
Thomann, et al., J of Colloid and Interface Sciences, vol. 157 pp. 369-374 (1993).
West et al., Journal of Dentistry, 1999(27), pp. 341-344.
van der Reijden, et al., Caries Res, 1997 31 pp. 216-223.
van Loveren, et al., Nutrition and Denatal Diseases, pp. 109-110 (1995).

* cited by examiner

ORAL COMPOSITIONS COMPRISING A VISCOSITY MODIFIER FOR REDUCTION OF TOOTH EROSION

The present invention relates to the use of thickening agents and stabilisers in acidic compositions for oral use such as foodstuffs and oral healthcare compositions to alleviate or inhibit the tooth damage associated with the consumption of acid, namely dental erosion.

Dental erosion describes the "pathologic, chronic, localised, painless loss of dental hard tissue chemically etched away from the tooth surface by acid and/or chelation without bacterial involvement" (Imfeld, 1996). The acids causing the erosion are derived from dietary, occupational or intrinsic sources and are not products of the intraoral flora. With the trend towards an increase in eating and drinking frequency amongst all age groups it is likely that the incidence of dental erosion will increase.

International Patent Publication (WO 97/30601) describes acid-based liquid compositions having reduced tooth erosion properties in which calcium is present in the range of 0.3 to 0.8 mol per mol of acid and which have a pH in the range 3.5 to 4.5.

Complex polysaccharide gums and other natural or synthetic polymers having viscosity modulating properties are routinely added to beverages, other foodstuffs and oral products as thickeners, stabilisers, emulsifiers and texturisers. These polymers include natural and semi-synthetic polymer materials such as alginates, locust bean gum, gellan gum, guar gum, gum arabic, xanthan gums, pectins, cellulose, and derivatives thereof; synthetic polymers such as polyvinylpyrrolidone (PVP) and other such materials known in the art.

Van der Reijden et al (Caries Res., 1997, 31, 216-23) describes a range of in vitro experiments with saliva substitute compositions containing thickening agents to investigate their caries-protective properties, including the effect on demineralisation and remineralisation of enamel in vitro. The effect of a range of polymer materials on dissolution of hydroxyapatite crystals in 50 mM acetic acid at pH 5.0, and a pH cycling experiment in which bovine enamel is exposed to demineralisation buffer (pH 4.8) and to remineralisation buffer (pH 7.0) containing a range of dissolved polymers, are described.

It has now been found that the addition of natural and synthetic polymer materials having stabilising, emulsifying and/or thickening properties to acidic foodstuffs and oral healthcare compositions reduces tooth erosion due to the loss of calcium and phosphate from tooth enamel generally associated with such products.

Furthermore, it has surprisingly been found that addition of one or more such polymer materials and calcium to an acidic composition for oral use reduces the loss of calcium and phosphate from tooth enamel to a greater extent than is conferred by addition of either polymer or calcium alone. Acidic compositions for oral use which are palatable, storage stable and effective in reducing dental erosion due to acid may accordingly be formulated with less calcium per mole of acid and at lower pH values than are disclosed in WO 97/30601

Accordingly, the present invention provides the use of a viscosity modulating polymer material as a tooth erosion inhibitor in an acidic composition for oral administration wherein the effective pH of the composition is less than or equal to 4.5.

In a further aspect the invention provides a composition for oral use comprising an acidulant, a viscosity modulating polymer material and a calcium compound wherein calcium is present in the composition in an amount up to 0.8 mol per mol of acid and the effective pH of the composition is less than or equal to 4.5.

The effective pH of compositions for oral use according to the invention will vary according to type of product, acid content and desired organoleptic properties. Suitably compositions for use in the invention will have an effective pH in the range 2.0 to 4.5, more suitably from 2.5 to 4.5, and preferably in the range 2.5 to 4.0, especially for beverages containing fruit acids.

Suitable viscosity modulating polymer materials for use in compositions of the invention include food grade complex polysaccharide stabilisers and thickening agents such as alginates, locust bean gum, gellan gum, guar gum, gum arabic, tragacanth, carrageenan, acacia gum, xanthan gums, pectins, cellulose derivatives and other such natural or semi-synthetic polymer materials used in the field of foodstuffs and other compositions for oral use, including mixtures of one or more thereof. A suitable synthetic, non-polysaccharide viscosity modulating polymer is polyvinylpyrrolidone (PVP).

Preferred complex polysaccharide materials for use in the invention include alginates, xanthans and pectins, in particular high methoxy pectins, low ester pectins and amidated or partly amidated pectins. Suitable alginates include commercially available low, medium and high viscosity alginate products. For example, low viscosity propylene glycol alginate and sodium alginate sold under the trade names Kelcoloid LVF and Manucol LF by Monsanto; medium viscosity sodium alginate sold under the trade name Manucol DH by Monsanto; and high viscosity propylene glycol alginate sold under the trade name Kelcoloid HVF by Monsanto. Suitable xanthans include a range of products available from Monsanto under the trade names Keltrol T, Keltrol RD, Keltrol TF, Keltrol SF and Keltrol BT. Suitable pectins include high methoxy pectins such as Unipectin QC40 available from SKW Biosystems; low ester pectins such as products sold under the trade names GENU LM 22 CG and GENU LM 12 CG, partly amidated low ester pectins such as products sold under the trade names GENU LM 101 AS and GENU LM 102 AS, and amidated low ester pectins such as the product sold under the trade name GENU LM 104 AS FS, all of which pectin products are available from Hercules Ltd.

It has been shown that inhibition of dental erosion increases with increasing concentration of a given polymer material. However, viscosity is not the primary factor influencing anti-erosive potential; experiments comparing the effect of different types of polymer materials at the same viscosity have shown that they inhibit dental erosion to different extents, especially at low viscosities typical of beverage formulations. Polymer materials for use in the invention may therefore be selected and used at concentrations which may be calculated to confer a viscosity commensurate with the required product type, ranging from liquid products such as acidic drinks through to semi-solid and solid acidic products. For example, a typical low viscosity product such as a beverage composition may incorporate a suitable polymer material at a concentration calculated to confer a viscosity below about 10 cP, preferably below about 6 cP. It will be appreciated that viscosity values are not absolute but are dependent on the conditions under which they are measured. Where exact values are relied on herein, the equipment used and the conditions under which it is operated are quoted.

The invention is accordingly applicable to all acidic products for oral consumption or use. These include acidic beverages, vinegars, sauces, pickles, preserves, confectionery and diverse acidic products such as acidic dairy products, and also to other substances, suitably in liquid or semi-solid form, to be taken orally such as acidic oral healthcare products, for example mouth washes, and medicines.

The invention may be applied to a variety of solid, semi-solid or liquid foodstuffs, particularly acidic beverages. These include still and carbonated alcoholic and non-alcoholic beverages, for example fruit drinks, and in particular health drinks such as blackcurrant juice drinks or vitamin added beverages. The invention also extends to concentrates and powdered forms for preparing acidic beverages. In a preferred embodiment, the acid composition is a ready to drink beverage or a drink concentrate for dilution prepared from a natural fruit juice such as blackcurrant juice.

The invention is advantageously applied to acidic compositions, in particular foodstuffs and especially beverages, containing natural and/or added acidulants. The acid composition may contain organic and/or inorganic acids and may be supplemented with vitamins such as ascorbic acid. Preferred acidulants include potable acids such as citric, malic, lactic, phosphoric, acetic and tartaric acids and mixtures thereof.

The acidulant concentration in a composition according to the invention will be determined by the type of product, the desired effective pH, the desired organoleptic properties and the acidity of the chosen acid source. The acidity of a composition may be expressed in terms of titratable acidity which is a measure of the percentage weight of acid present in a solution as calculated from the volume of sodium hydroxide required to neutralise the acidic species present. In practice, titratable acidity is measured potentiometrically with standardised sodium hydroxide solution of a known concentration at a temperature of 20 degrees Centigrade. A typical beverage will have a titratable acidity in the range 0.01 to 4% w/w and a typical fruit-based ready to drink beverage will have a titratable acidity in the range 0.1 to 2% w/w. Typically the acid concentration in compositions of the invention, for example the acid concentration in a fruit-based product would be in the range 0.01% w/w to 4% w/w, suitably in the range 0.1% w/w to 2.5% w/w. A typical ready to drink fruit beverage based on citric and/or malic acid as the acidulant will have an acid concentration in the range 0.01 to 1.0% w/w of the beverage composition. In a concentrate for dilution, typical citric/malic acid concentration will be in the range 0.1 to 4% w/w of the composition. Mixtures of potable acids may be used, for example mixtures of acids selected from citric, malic, phosphoric and lactic acids and other suitable food grade excipients known in the art.

Foodstuffs such as beverages may be unsweetened or sweetened with natural sugars or synthetic sweeteners such as saccharine, aspartyl phenyl alanyl methyl ester, or other sweeteners known in the art. Compositions may also contain other conventional additives such as sodium benzoate, sorbic acid, sodium metabisulfite, ascorbic acid, flavourings, colorings and carbon dioxide.

The term effective pH is used in the context of the present invention to mean the pH of the composition when in liquid form or the pH of the composition before solidification (where the composition is a solid or semi-solid prepared via a liquid phase intermediate) or the pH of a solid or semi-solid composition when reconstituted or dissolved in a liquid, eg. water. The term solidification encompasses the treatment or supplementation of liquid phase intermediates to form a solid or semi-solid.

A further advantage arises from the use of low levels of calcium, suitably in the form of an alkaline salt. When calcium is present, the buffering capacity of the formulation is reduced by partial neutralisation of the acid, which allows saliva to neutralise remaining acid residues in the mouth more rapidly.

When calcium is present, the absolute concentration is not critical as this will vary according to the nature and concentration of the acids present. Calcium may be added in any suitable form, conveniently as a soluble salt such as calcium carbonate, calcium hydroxide, calcium citrate, calcium malate, calcium citrate malate, calcium lactate, calcium chloride, calcium phosphate, calcium glycerophosphate or calcium formate or any other salt which minimises any adverse flavour contribution to the composition. Calcium content is suitably calculated on a molar basis relative to the molarity of the acidulant. Calcium may be present in an amount up to 0.8 mol per mol of acidulant. The molar ratio of calcium to acid may be from 0.01 to 0.75, is likely to be from 0.05 to 0.6, and typically from 0.1 to 0.5 for a fruit-based beverage product.

In a further aspect, the present invention provides a method of reducing the tooth erosion potential of an acidic composition for oral use comprising adding a viscosity modulating polymer material, and optionally calcium in the range 0 to 0.8 mol per mol of acid, to an acidic oral composition and, if necessary or desired, controlling the effective pH so that it is less than or equal to 4.5.

For the avoidance of doubt, the phrase 'if necessary or desired' encompasses control of pH to bring it into the defined range as well as control of pH within the defined range. The effective pH of the formulation may be adjusted to the desired value by the addition of alkali, eg. a soluble alkaline salt such as sodium hydroxide or sodium citrate, sodium malate or sodium lactate and by the addition of calcium when present.

The invention also extends to a method of reducing tooth erosion caused by acid in orally administered compositions by orally administering a composition comprising a viscosity modulating polymer material and an acidulant, and optionally containing calcium in the range 0 to 0.8 mol per mol of acid, wherein the effective pH of the composition is less than or equal to 4.5.

The invention further extends to the use of a composition comprising a viscosity modulating polymer material and an acidulant, optionally containing calcium in the range 0 to 0.8 mol per mol of acid, and having a pH less than or equal to 4.5, in the manufacture of a medicament for the reduction of tooth erosion caused by acid in orally administered compositions.

Oral compositions may contain magnesium or other ions as adjuncts for remineralisation. They may also contain an effective amount of malic acid or potable salts thereof to maintain the solubility of calcium, when present, so as to prevent or minimise the precipitation of insoluble calcium salts. Added malic acid will contribute to the total acidity of the beverage, the remainder of the acidity being provided by other, preferably naturally present, acids such as citric acid, lactic acid and tartaric acid.

Oral compositions may be prepared by mixing the ingredients according to conventional methods. Solid ingredients may be dissolved in aqueous media, eg. water, with heating if required prior to addition to other components. Viscosity modulating polymer materials such as complex polysaccharides are generally hydrated in aqueous media with high shear mixing before addition. Typically beverages and other liquid products are pasteurised prior to filling in bottles or cans or other packs or are "in-pack pasteurised" after filling.

The following examples are illustrative of the invention. Commercial sources for the food grade polymers used in all experiments are as follows:

Xanthan gums sold under trade names Keltrol T, Keltrol RD, Keltrol TF. Keltrol SF, Keltrol BT from Monsanto, Tadworth, Surrey, UK. Xanthan polymer from IFF, Haverhill, Suffolk, UK. Xanthan gum, guar and tragacanth from Thew Arnott & Co. Ltd, Wallington, Surrey, UK. Xanthan gum sold under trade name Satiaxane and xanthan/guar mixture sold under trade name Lygomme MM391 from SKW Biosystems, Newbury, Berkshire, UK. Xanthan/sodium carboxymethylcellulose (35/65% w/w) mixture sold under trade name Grinstead JU543 from Danisco Ingredients Ltd, Bury St Edmunds. UK. Acacia gum, propylene glycol alginate and sodium carboxymethylcellulose from Red Carnation gums Ltd, Laindon, Essex, UK. Blanose cellulose gum (9M31XF) from Hercules Ltd, Reigate, Surrey, UK. Alginate polymers sold under trade names Kelcoloid LVF, Kelcoloid HVF, Manucol DH and Manucol LF from Monsanto, Tadworth, Surrey, UK. Iota carrageeenan sold under trade name Genuvisco type J and pectins sold under trade names GENU LM 102 AS, GENU LM 104 AS, GENU LM 101 AS, GENU LM 22 CG, GENU LM 12 CG and GENU-VIS from Hercules Ltd, Reigate, Surrey, UK. Pectin sold under trade name Unipectin QC40 from SKW Biosytems, Newbury, Berkshire, UK. Polyvinylpyrrolidone sold under the trade name PVP K30 by ISP, NJ, USA.

EXAMPLE 1

A commercially available ready to drink beverage (pH 3.5) approximating to the following formulation was tested against a control beverage prepared without the addition of xanthan gum.

| Ingredients | Quantity |
| --- | --- |
| Orange juice | 110 L |
| Citric Acid | 3.8 Kg |
| Acesulfame K | 0.74 Kg |
| Aspartame | 0.72 Kg |
| Ascorbic Acid | 0.29 Kg |
| Orange Flavouring | 0.4 L |
| Xanthan Gum (Keltrol T) | 0.34 Kg |
| Water to 1000 L | |

The two beverages were tested for their potential to dissolve enamel in the in vitro protocol detailed below in which flat dental enamel sections were exposed to test solutions at a temperature of 37° C. for 4 hours. Erosive potential was evaluated by physical measurement of the depth of enamel lost during the procedure. The control beverage without the thickening agent gave an enamel loss of 16 μm over the 4 hour exposure period as compared to the beverage with xanthan gum which gave an enamel loss of 1 μm.

Protocol for the Determination of In Vitro Enamel Loss

The erosive potential of the test solutions was determined by measuring the in vitro enamel loss over 4 hours in the manner described by Davis & Winter (Davis W B, Winter P J, British Dental Journal, 1977, 143, 116-119) and West et al (West N X et al., J Dentistry, 1998, 26(4), 329-335). Recently extracted, caries free, wisdom teeth were sectioned and mounted in epoxy resin blocks with buccal aspect uppermost. The enamel samples were ground, removing a minimum amount of enamel to produce a flat, level block. Baseline measurements were recorded by surfometry and the area to be exposed delineated by the application of PVC tape. 6 masked enamel specimens were exposed to 200 mL of test solution for 4×1 hour time periods at 37° C. with overhead stirring. The test solution was replaced hourly. The enamel samples were subsequently rinsed with deionised water, the PVC tape removed and the tissue loss assessed by surfometry.

EXAMPLE 2

1000 Kg of a powdered orange sports drink was prepared by mixing the following ingredients:

| Ingredient | Quantity (Kg) |
| --- | --- |
| Dextrose monohydrate | 400 |
| Maltodextrin | 538 |
| Aspartame | 0.6 |
| Acesulfame k | 0.38 |
| Sodium citrate | 17.0 |
| Citric acid | 38.0 |
| Ascorbic acid | 1.2 |
| Potassium citrate | 2.4 |
| Vitamin Premix (B2, B6, B12, Niacin, Pantothenic acid) | 0.4 |
| Orange flavour | 3.0 |
| Beta-Carotene (1%) | 6.0 |
| Blancse Cellulose Gum (9M31XF) | 1.0 |

A beverage (pH 3.4) was prepared for consumption by dilution of the powder (50 g) in water (500 mL).

EXAMPLE 3

Solutions of citric acid were prepared in deionised water and adjusted to pH 3.8 with 0.1 M sodium hydroxide solution. Calcium was added in the form of calcium carbonate and/or xanthan gum was added as Keltrol T. All solutions were tested in a 4 hour in vitro protocol as described in Example 1.

| | Results | | |
| --- | --- | --- | --- |
| Citric Acid Monohydrate (CAMH)(% w/v) | Xanthan Gum (% w/v) | Ca/CAMH Mol Ratio | 4 hr Enamel Loss (μm) |
| 0.3 | 0 | 0 | 7.6 |
| 0.3 | 0.034 | 0 | 5.3 |
| 0.3 | 0 | 0.3 | 5.4 |
| 0.3 | 0.034 | 0.3 | 2.8 |

EXAMPLE 4

Screening of Food Grade Thickening Agents for Inhibition of Dental Erosion

Solutions were prepared using a sufficient mass of thickening agent to give a solution of 5-6 cP at 50 rpm (shear rate 61.2 s$^{-1}$), 37° C. using a Brookfield LVDVII+ viscometer fitted with a UL adaptor. Citric acid buffer was prepared in deionised water using citric acid monohydrate (AR grade, BDH Merck Ltd), preserved with sodium benzoate (0.16 g/L, AR grade, BDH Merck Ltd). All Thickening agents were hydrated in buffer by blending for 2 mins using a Silverson high shear mixer, except for guar gum which was stirred overnight at 1000 rpm using a magnetic stirrer. Mixtures of thickening agents were prepared by dry blending prior to hydration. All solutions prepared to give a pH of 3.40 and titratable acidity of 0.3% w/v CAMH. (Citric acid monohydrate). Buffered citric acid (0.3% w/v CAMH, pH 3.40) solution was used as control. Solutions were tested in a 4 hour in vitro protocol as described in Example 1.

| Thickening Agent | Trade Name (Supplier) | Thickener Conc. (% w/v) | 4 Hr Enamel Loss (μm) | SD (μm) |
|---|---|---|---|---|
| Xanthan (clarified) | Keltrol T | 0.07 | 9.8 | 2.2 |
| Xanthan | (IFF) | 0.07 | 14.7 | 1.2 |
| Xanthan (clarified dispersible) | Keltrol RD | 0.07 | 6.6 | 0.8 |
| Xanthan | (Thew Arnott Co. Ltd) | 0.07 | 9.7 | 1.2 |
| Xanthan (fine mesh) | Keltrol TF | 0.07 | 8.3 | 0.8 |
| Xanthan | Satiaxane | 0.07 | 14.1 | 1.6 |
| Xanthan (smooth flow) | Keltrol SF | 0.1 | 7.2 | 1.3 |
| Xanthan(clarified/salt tolerant) | Keltrol BT | 0.07 | 10.7 | 2.4 |
| Xanthan/Guar | Lygomme MM391 | 0.22 | 14.7 | 1.7 |
| Xanthan/Sodium carboxymethylcellulose | Grinstead JU543 | 0.12 | 13.6 | 2.1 |
| Acacia gum | (Red Carnation Gums) | 10.5 | 13.7 | 1.5 |
| Propylene Glycol Alginate (low viscosity) | Kelcoloid LVF | 0.59 | 4.8 | 0.3 |
| Propylene Glycol Alginate | (Red Carnation Gums) | 0.45 | 6.9 | 1.8 |
| Propylene Glycol Alginate (high viscosity) | Kelcoloid HVF | 0.39 | 6.3 | 1.0 |
| Sodium Alginate (medium viscosity) | Manucol DH | 0.55 | 2.6 | 0.9 |
| Sodium Alginate (low viscosity) | Manucol LF | 0.75 | 2.9 | 0.5 |
| Guar | (Thew Arnott Co. Ltd) | 0.18 | 11.1 | 1.2 |
| Tragacanth | (Thew Arnott Co. Ltd) | 0.22 | 11.0 | 1.8 |
| Iota Carrageenan | Genuvisco type J | 0.375 | 2.7 | 0.6 |
| High Methoxy Pectin | Unipectin QC40 | 1 | 9.9 | 1.1 |
| Partly Amidated Low Ester Pectin (citrus peel) | GENU LM 102 AS | 1 | 1.6 | 0.3 |
| Amidared Low Ester Pectin (citrus peel) | GENU LM 104 AS | 1 | 0.7 | 0.4 |
| Partly Amidated Low Ester Pectin (citrus peel) | GENU LM 101 AS | 1.1 | 2.0 | 0.8 |
| Low Ester Pectin (citrus peel) | GENU LM 22 CG | 1.2 | 5.7 | 0.6 |
| Low Ester Pectin (citrus peel) | GENU LM 12 CG | 1.1 | 1.4 | 0.6 |
| Propylene Glycol Alginate/Low Methoxy Amidated Pectin (50:50) | Kelcoloid LVF & GENU LM 102 AS | 0.54 | 1.53 | 0.58 |
| Propylene Glycol Alginate/Xanthan (66.6:33.3) | Kelcoloid LVF & Keltrol RD | 0.15 | 7.57 | 0.45 |
| Control | — | — | 24.5 | 1.9 |
| Control | — | — | 20.8 | 2.0 |
| Control | — | — | 24.1 | 3.8 |
| Control | — | — | 30.5 | 3.17 |
| Control | — | — | 19.9 | 1.53 |
| Control | — | — | 29.9 | 1.53 |

EXAMPLE 5

Effect of Addition of Thickening Agent Over Range of pH and Acidity Values on Inhibition of Dental Erosion Solutions were prepared to represent the range of pH and acidity values typically found in a soft drink. Solutions were prepared by shearing the required mass of thickening agent in citric acid buffer, preserved with sodium benzoate (0.16 g/L), for 2 minutes using a Silverson high shear mixer. The pH was adjusted to the required value by the addition of 1 M NaOH. All solutions gave viscosity values of 5 to 6 cP (Brookfield LVDVII+ UL adaptor, 50 rpm, 37° C.). Solutions were tested in a 4 hour in vitro protocol as described in Example 1. The results demonstrate the efficacy of the technology in reducing enamel loss over a range of pH values and viscosities.

| Thickening Agent | Th.Conc. (% w/v) | pH | Acidity (% w/w CAMH) | 4 Hr Enamel Loss (μm) | SD (μm) |
| --- | --- | --- | --- | --- | --- |
| Control | — | 2.5 | 0.1 | 63.4 | 4.4 |
| Keltrol RD | 0.07 | 2.5 | 0.1 | 8.7 | 1.2 |
| Keltrol RD | 0.07 | 2.5 | 0.3 | 9.7 | 1.2 |
| Kelcoloid LVF | 0.59 | 2.5 | 0.3 | 11.5 | 3.6 |
| Control | — | 2.5 | 0.3 | 41.04 | 0.2 |
| Control | — | 2.5 | 0.3 | 30.4 | 6.1 |
| Keltrol RD | 0.07 | 3.0 | 0.7 | 13.5 | 1.6 |
| Control | — | 3.0 | 0.7 | 34.2 | 3.8 |
| Kelcoloid LVF | 0.55 | 3.0 | 0.3 | 11.6 | 3.0 |
| Keltrol RD | 0.07 | 3.0 | 0.3 | 7.84 | 1.1 |
| Control | — | 3.0 | 0.3 | 23.2 | 0.4 |
| Control | — | 3.0 | 0.3 | 26.3 | 2.5 |
| Keltrol RD | 0.07 | 4.5 | 1.0 | 7.1 | 1.3 |
| Kelcoloid LVF | 0.59 | 4.5 | 1.0 | 11.4 | 1.0 |
| Control | — | 4.5 | 1.0 | 21.2 | 1.8 |

EXAMPLE 6

Determination of the Effect of Viscosity and Type of Thickening Agent on In Vitro Enamel Loss Viscosity versus concentration plots were determined for two commercially available food gums, a high ester citrus pectin (GENUVIS) and finely milled xanthan gum (Keltrol T). Gums were hydrated in a 0.3% w/v citric acid monohydrate buffer, adjusted to pH 3.4 with 1M NaOH. A controlled strain Rheometrix RFSII viscometer (with cuette geometry) was run at 37° C. and concentration v viscosity plots produced using a shear rate of 125 s$^{-1}$. Concentrations of the two gums were determined to give viscosity values of 2.5 cP, 5.0 cP, 10 cP and 20 cP under the conditions used. A viscosity v concentration profile for a sodium carboxymethyl cellulose gum (Red Carnation gums Ltd) was determined using a Brookfield LVDVII+ viscometer (fitted with a UL adaptor at 60 rpm (104 s$^{-1}$) at 37° C.). The approximate concentration required to give a viscosity of 20 cP under these conditions was estimated by extrapolation from the plot. Solutions were tested for in vitro enamel loss using the screening protocol described in Example 1.

| | | | | Results | | |
| --- | --- | --- | --- | --- | --- | --- |
| Viscosity (cP) | % w/v xanthan | % w/v pectin | % w/v CMC | 4 Hr Enamel loss- xanthan (μm) | 4 Hr Enamel loss- pectin (μm) | 4 Hr Enamel loss- CMC (μm) |
| 2.5 | 0.05 | 0.67 | — | 8.7 | 11.5 | — |
| 5 | 0.08 | 0.9 | 0.17 | 7.8 | 12.0 | 31.0 |
| 10 | 0.14 | 1.20 | — | 2.3 | 9.0 | — |
| 20 | 0.24 | 1.6 | 0.39 | 2.5 | 2.7 | 13.5 |

Low-methoxy amidated pectin (GENU LM 102 AS) and low viscosity propylene glycol alginate (Kelcoloid LVF) were tested in the model of erosive potential at different concentrations. Each solution of gum was hydrated using a 0.3% w/v citric acid monohydrate buffer at pH 3.40. Viscosities were determined using a Brookfield LVDVII+ viscometer (fitted with a UL adaptor) at 50 rpm (shear rate 61.2 s$^{-1}$) and 37° C.

| GENU LM 102 AS (% w/v) | Viscosity (cP) | 4 Hr Enamel Loss (μm) |
| --- | --- | --- |
| 1.0 | 5.7 | 1.6 |
| 0.75 | 3.8 | 3.4 |
| 0.5 | 2.3 | 1.0 |

| Kelcoloid LVF (% w/v) | Viscosity (cP) | 4 Hr Enamel Loss (μm) |
| --- | --- | --- |
| 0.59 | 6.7 | 4.8 |
| 0.45 | 3.5 | 6.7 |

The results confirm that viscosity is not the primary factor influencing erosive potential in this model. A general decrease in enamel loss was found with increasing viscosity for each material tested but enamel losses were not equivalent, suggesting that erosive potential is product type specific, particularly at viscosity values of 10 cP or less which are most suitable for the formulation of acidic compositions with low erosive potential.

EXAMPLE 7

Effect of Thickening Agent and Calcium on Dental Erosion

Test formulations of typical pH and acidity for a ready to drink fruit beverage were prepared using stock solutions of citric acid buffer (300 g/L) and sodium benzoate preservative (16 g/L). Solutions were blended for 2 minutes using a Silverson high shear mixer. Viscosities were determined using a Brookfield LVDVII+ viscometer (fitted with a UL adaptor) at 50 rpm (shear rate 61.2 s$^{-1}$) and 37° C. Solutions were tested for in vitro enamel loss using the screening protocol described in Example 1. The results show that addition of a thickening agent and calcium to acid compositions confers low erosive potential at calcium levels and pH values below those which are required in the absence of a thickening agent.

| Ingredient | Test Solution A | Test Solution B |
| --- | --- | --- |
| Deionised water | 800 ml | 800 ml |
| Benzoate stock solution | 20 ml | 20 ml |
| Xanthan gum (Keltrol RD) | 1.8 g | 2.0 g |
| Citric Acid stock solution | 20 ml | 120 ml |
| Calcium carbonate | 0.28 g | 0.157 g |
| Deionised water | to 1800 ml | to 1800 ml |
| 1M NaOH | to pH 3.40 | to pH 3.20 |
| Deionised water | to 2 L (volumetric) | to 2 L (volumetric) |

| Test Solution | Viscosity (cP) | pH | Titratable Acidity (% w/w CAMH) | Ca/Acid Ratio | 4 Hr Enamel Loss (μm) |
| --- | --- | --- | --- | --- | --- |
| A | 8 | 3.4 | 0.3 | 0.1 | 1.4 |
| B | 9 | 3.2 | 0.3 | 0.05 | 3.3 |

EXAMPLE 8

Ready to Drink Blackcurrant Juice Beverages

A base syrup was prepared as follows:

Sodium benzoate (0.80 g) was dissolved in warm treated water and diluted to approximately 200 ml with treated water. Blackcurrant concentrate (88.2 ml) was added followed by solutions of ascorbic acid (2.55 g) and aspartame (1.60 g), acesulfame K (0.50 g), and potassium sorbate (152 g), in treated water. Blackcurrant flavour (1.14 ml) was added to the mixing batch and the volume was corrected to 1 liter with treated water.

Two ready to drink beverage formulations were prepared as follows:

Thickening agent was added to water (2.5 liters) with stirring using a high shear Silverson mixer and mixing continued to form a solution. Calcium carbonate (where present) was dissolved in treated water and slowly added to the solution. Base syrup (1 liter) was added with mixing to form a homogenous solution and volume was adjusted to 5 liters with water. The pH was corrected with 3.4 with 1 M sodium hydroxide. Viscosity was measured using a Brookfield LVDII+ viscometer with UL adaptor at 50 rpm and 37 C. Titratable acidity for both formulations (% w/w CAMH) was 0.4. The formulations were tested for in vitro enamel loss using the screening protocol described in Example 1.

| Thickening Agent (g) | CaCO₃ (g) | Ca/Acid molar ratio | Viscosity (cP) | 4 Hr Enamel Loss (μm) |
| --- | --- | --- | --- | --- |
| Kelcoloid LVF (29.5) | — | — | 6.7 | 3.6 |
| Keltrol RD (4.5) | 0.7 | 0.1 | 7.6 | 6.2 |

EXAMPLE 9

Ready to Drink Sparkling Raspberry Flavoured Beverage

Pectin thickener (GENU LM 102 AS) (37.5 g) was sprinkled into warm water (1 liter) with high shear mixing using a Silverson mixer. Solutions of potassium sorbate (1.28 g), acesulfame K (0.27 g), citric acid (14.0 g) and aspartame (1.20 g) and ascorbic acid (1.50 g) and potassium citrate (4.81 g) were prepared separately and added to the pectin batch with mixing. Raspberry flavouring (2.51 ml), and cochineal red colour (0.50 ml) dispersed in water were added to the mix forming a base syrup which was diluted with water to 1.67 liters. The base syrup was diluted (1 part syrup to 2 parts water) with carbonated water to form a sparkling drink. Viscosity was measured using a Brookfield LVDII+ viscometer with UL adaptor at 50 rpm and 37 C. The product was tested for in vitro enamel loss using the screening protocol described in Example 1.

The product had the following parameters:

| pH | 3.5 |
| --- | --- |
| Acidity (% w/w CAMH) | 0.4 |
| Viscosity (cP) | 3.2 |
| Enamel loss (m) | 3.67 |

EXAMPLE 10

Ready to Drink Cola Flavoured Sparkling Beverage

A cola concentrate was made by mixing the following ingredients:

| Phosphoric acide 85% | 1 liter |
| --- | --- |
| Caffeine BP | 130 g |
| Cola emulsion | 0.75 liter |
| Caramel double strength | 3.125 liter |
| Water to | 10 liter |

A cola syrup was made by mixing the following ingredients:

| Sugar syrup 67 Brix | 70 liter |
| --- | --- |
| (or aspartame | 300 g) |
| Cola concentrate | 2.5 liter |
| Cola flavour booster | 0.06 liter |
| Xanthan (Keltrol RD) | 420 g |
| Water to | 100 liter |

The cola syrup was diluted (1 part syrup to 5 parts water) with carbonated water to form a sparkling drink with a pH of approximately 2.5.

EXAMPLE 11

Effect of Polyvinyl Pyrrolidone on Inhibition of Dental Erosion

Citric acid buffer (0.3% w/v citric acid monohydrate) was prepared in deionised water with the addition of sodium benzoate (0.16 g/L) as a preservative. The solution was adjusted to pH 3.4 with 1M NaOH. Polyvinylpyrolidone (PVP-K30, 125 g/L) was added to the solution with stirring and the resulting solution stirred for 20 minutes. This gave a solution of pH 3.4, titratable acidity 0.3% w/w CAMH, viscosity 4.7 cP (37° C., 50 rpm, Brookfield LVDVII+, UL adaptor). The solution was gave an enamel loss of 13.8 μm as compared to an enamel loss of 25 μm from a control buffer solution when tested over 4 hours in the in vitro erosivity screening protocol

EXAMPLE 12

Mouthwash Formulation

A mouthwash was prepared using from following ingredients:

| Ingredient | % w/w |
|---|---|
| Ethanol 96% BP | 8 |
| Soluble saccharin | 0.06 |
| Cetylpyridinium chloride | 0.05 |
| Tego Betain CK-KB5 | 0.2 |
| Flavouring | 0.12 |
| Sodium acetate trihydrate | 0.05 |
| Acetic acid 80% | 0.1575 |
| PVP-K30 | 12.5 |
| Calcium chloride dihydrate | 0.123 |
| Deionised water | 78.74 |

The ethanol, cetylpyridinium chloride, Tego Betain CK-KB5 (trade name for a cocamido propyl betaine) and flavouring were mixed together to form a clear solution. In a separate container, the remainder of the ingredients were mixed together and stirred for 20 minutes. The ethanolic solution was then added to the aqueous solution to produce a mouthwash with a pH of 4.5 and a calcium to acid molar ratio of 0.4.

The invention claimed is:

1. A method of reducing tooth erosion caused by acid in orally administered compositions comprising
   (i) providing a first acidic orally administrable composition;
   (ii) adding to said first acidic orally administrable composition:
      (a) a calcium compound present in an amount of 0.01 to 0.75 mol per mole of acid;
      (b) a viscosity modulating polymer material which is a polysaccharide selected from the group consisting of an alginate, locust bean gum, gellan gum, guar gum, gum arabic, tragacanth, carrageenin, acacia gum, xanthan gum, pectin, cellulose gum, or a combination or mixture thereof; and
      (c) controlling or adjusting the effective pH of the resulting composition to less than or equal to 4.5, and
   (iii) thereby providing a second acidic orally administrable composition which has a lower tooth erosion potential than said first acidic orally administrable composition; and
   (iv) orally administering said second acidic orally administrable composition to a mammal.

2. The method as claimed in claim 1 wherein the polysaccharide is an alginate, a xanthan gum or a pectin.

3. The method as claimed in claim 1 wherein the effective pH of the composition is from 2.0 to 4.5.

4. The method as claimed in claim 1 wherein the acid in the first or second acidic composition is citric acid, malic acid, lactic acid, tartaric acid, phosphoric acid, acetic acid or a mixture thereof.

5. The method as claimed in claim 1 wherein the calcium compound present in the composition has a molar ratio of calcium to acid from 0.1 to 0.5.

6. The method as claimed in claim 1 wherein the calcium compound is a soluble calcium salt.

7. The method as claimed in claim 1 wherein the second acidic composition is a beverage or a liquid or solid concentrate for the preparation of a beverage.

8. The method as claimed in claim 7 wherein the beverage is a health drink.

9. The method as claimed in claim 1 wherein the second acidic composition is an oral healthcare product.

10. The method as claimed in claim 7 wherein the beverage has a pH in the range 2.5 to 4.0.

11. The method as claimed in claim 7 wherein the beverage has a titratable acidity in the range 0.01 to 4% w/w.

12. A process for preparing an acidic orally administrable composition comprising;
   (i) providing a first acidic orally administrable composition;
   (ii) adding to said first acidic orally administrable composition:
      (a) a viscosity modulating polymer material selected from the group consisting of an alginate, locust bean gum, gellan gum, guar gum, gum arabic, tragacanth, carrageenin, acacia gum, xanthan gum, pectin, cellulose gum, or a combination or mixture thereof;
      (b) calcium in the range 0.01 to 0.8 mol per mol of acid;
      (c) adjusting or controlling the effective pH provide a composition with an effective pH less than or equal to 4.5;
   (iii) thereby providing a second acidic composition which has a lower tooth erosion potential than said first acidic orally administrable composition.

13. A process for preparing an acidic orally administrable composition comprising:
   (i) providing a first acidic orally administrable composition;
   (ii) adding to said first acidic orally administrable composition:
      (a) a viscosity modulating polymer material which is polyvinylpyrrolidone;
      (b) calcium in the range 0 to 0.8 mol per mol of acid; and
      (c) controlling or adjusting the effective pH to provide a composition with an effective pH less than or equal to 4.5;
   (iii) thereby providing a second acidic composition which has a lower tooth erosion potential than said first acidic orally administrable composition.

14. A method of reducing tooth erosion caused by acid in orally administered compositions comprising
   (i) providing a first acidic orally administrable composition;
   (ii) adding to said first acidic orally administrable composition:
      (a) a viscosity modulating polymer material which is polyvinylpyrrolidone;
      (b) and optionally adding calcium in the range 0 to 0.8 mol per mol of acid; and
      c) controlling or adjusting the effective pH to provide a composition with an effective pH less than or equal to 4.5;
   (iii) thereby providing a second acidic composition which has a lower tooth erosion potential than said first acidic orally administrable composition;
   (iv) orally administering said second acidic orally administrable composition to a mammal.

15. The method as claimed in claim 1 wherein the polysaccharide is present in an amount of 0.07 to 1.2% w/v.

16. The process as claimed in claim 12 wherein the viscosity modulating polymer material is an alginate, a xanthan or a pectin.

17. The process as claimed in claim 12 wherein the effective pH of the composition is from 2.0 to 4.5.

18. The process as claimed in claim 12 wherein the acid in the first or second acidic composition is citric acid, malic acid, lactic acid, tartaric acid, phosphoric acid, acetic acid or a mixture thereof.

19. The process as claimed in claim 12 wherein the calcium present in the composition has a molar ratio of calcium to acid from 0.1 to 0.5.

20. The process as claimed in claim 12 wherein the calcium present in the composition is a soluble calcium salt.

21. The process as claimed in claim 12 wherein the second acidic composition is a beverage or a liquid or solid concentrate for the preparation of a beverage.

22. The process as claimed in claim 12 wherein the beverage has a titratable acidity in the range 0.01 to 4% w/w.

23. The process as claimed in claim 13 wherein the effective pH of the composition is from 2.0 to 4.5.

24. The process as claimed in claim 13 wherein the acid in the first or second acidic composition is citric acid, malic acid, lactic acid, tartaric acid, phosphoric acid, acetic acid or a mixture thereof.

25. The process as claimed in claim 13 wherein the calcium present in the composition has a molar ratio of calcium to acid from 0.1 to 0.5.

26. The process as claimed in claim 13 wherein the calcium present in the composition is a soluble calcium salt.

27. The process as claimed in claim 13 wherein the second acidic composition is a beverage or a liquid or solid concentrate for the preparation of a beverage.

28. The process as claimed in claim 27 wherein the beverage has a titratable acidity in the range 0.01 to 4% w/w.

29. The method as claimed in claim 14 wherein the effective pH of the composition is from 2.0 to 4.5.

30. The method as claimed in claim 14 wherein the acid in the first or second acidic composition is citric acid, malic acid, lactic acid, tartaric acid, phosphoric acid, acetic acid or a mixture thereof.

31. The method as claimed in claim 14 wherein the calcium present in the composition has a molar ratio of calcium to acid from 0.1 to 0.5.

32. The method as claimed in claim 14 wherein the calcium present in the composition is a soluble calcium salt.

33. The method as claimed in claim 14 wherein the second acidic composition is a beverage or a liquid or solid concentrate for the preparation of a beverage.

34. The method as claimed in claim 33 wherein the beverage is a health drink.

35. The method as claimed in claim 14 wherein the second acidic composition is an oral healthcare product.

36. The method as claimed in claim 35 wherein the beverage has a pH in the range 2.5 to 4.0.

37. The method as claimed in claim 33 wherein the beverage has a titratable acidity in the range 0.01 to 4% w/w.

* * * * *